United States Patent
Ohya et al.

(10) Patent No.: US 8,118,985 B2
(45) Date of Patent: Feb. 21, 2012

(54) GAS SENSOR

(75) Inventors: Seiji Ohya, Aichi (JP); Tomohiro Wakazono, Konan (JP); Takashi Nakao, Kasugai (JP); Hisashi Sasaki, Konan (JP); Koji Shiotani, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 406 days.

(21) Appl. No.: 12/417,074

(22) Filed: Apr. 2, 2009

(65) Prior Publication Data

US 2009/0250344 A1     Oct. 8, 2009

(30) Foreign Application Priority Data

Apr. 2, 2008  (JP) ................... 2008-095640
Feb. 19, 2009 (JP) ................... 2009-036296

(51) Int. Cl.
 *G01N 27/41* (2006.01)
(52) U.S. Cl. ........ 204/426; 204/424; 204/427; 204/428; 204/429
(58) Field of Classification Search .......... 204/424, 204/426, 427, 428, 429
 See application file for complete search history.

(56) References Cited

U.S. PATENT DOCUMENTS

| | | | |
|---|---|---|---|
| 6,261,429 B1 * | 7/2001 | Jach et al. | 204/427 |
| 6,287,439 B1 | 9/2001 | Kato et al. | |
| 6,332,965 B1 | 12/2001 | Sugiyama et al. | |
| 2004/0111868 A1 * | 6/2004 | Katafuchi et al. | 29/592.1 |
| 2005/0161324 A1 | 7/2005 | Springhorn et al. | |
| 2007/0084723 A1 * | 4/2007 | Mizutani et al. | 204/424 |

FOREIGN PATENT DOCUMENTS

| | | |
|---|---|---|
| DE | 19827469 A1 | 1/1999 |
| EP | 0880026 A1 | 11/1998 |
| EP | 0884587 A1 | 12/1998 |
| EP | 1217365 A2 | 6/2002 |
| JP | 10-318979 A | 12/1998 |
| WO | 03/060502 A1 | 7/2003 |

* cited by examiner

*Primary Examiner* — Bruce Bell
(74) *Attorney, Agent, or Firm* — Sughrue Mion, PLLC (57) ABSTRACT

A gas sensor (200) has a gas sensor element (10) including a first measurement chamber (16); a first pumping cell (11) having a first interior pump electrode (11*c*) and its counterpart electrode (11*b*); a second measurement chamber (18); a second pumping cell (13) that has a second interior pump electrode (13*b*); and a heater (50). The heater (50) has a lead section (50*a*); a first resistance portion (50*bx*) having a higher resistance than the lead portion (50*a*); and a main heating portion (50*k*) having a second resistance portion (50*by*) having a higher resistance than the first resistance portion (50*bx*) disposed at a leading end side in a longitudinal direction relative to a leading end of the first resistance portion (50*bx*). The second interior pump electrode (13*b*) is located within the first resistance portion (50*bx*) in the longitudinal direction.

8 Claims, 8 Drawing Sheets

GAS SENSOR

BACKGROUND OF THE INVENTION

1. Field of the Invention

The present invention relates to a gas sensor having a gas sensor element for detecting the concentration of a specific gas, such as NOx, contained in a combustion gas or an exhaust gas from, for instance, a combustor or an internal combustion engine.

2. Description of the Related Art

As regulation of exhaust gas from an internal combustion engine, such as an automobile, is tightened, there has been a need to reduce the quantity of nitrogen oxides (NOx) in the exhaust gas. Further, an NOx sensor capable of directly measuring the concentration of NOx has been developed.

The NOx sensor has a gas sensor element. The gas sensor element has one or a plurality of cells, each of which comprises a pair of electrodes formed on a surface of a solid electrolytic layer exhibiting oxygen ion conductivity, such as zirconia. An oxygen concentration detection cell measures the concentration of oxygen in a first measurement chamber in mutual communication with a space for a gas to be measured. A first pumping cell controls (pumps in or pumps out) oxygen in the first measurement chamber such that a target oxygen concentration is achieved in the first measurement chamber. Moreover, a gas to be measured having a controlled oxygen concentration flows from the first measurement chamber to a second measurement chamber. A constant voltage is applied to a second pumping cell, whereby NOx contained in the gas to be measured in the second measurement chamber is decomposed into $N_2$ and $O_2$. At this time, a second pump current flowing between a pair of electrodes of the second pumping cell is measured, whereby the concentration of NOx in the gas to be measured is detected.

In such an NOx sensor, even when the concentration of NOx is zero, the second pump current comes to a predetermined current value (a so-called offset value). Hence, the concentration of NOx is converted by subtracting the offset value from the second pump current. Incidentally, there is a problem in that the offset value itself varies with a change in the temperature of the NOx sensor or the like, to thus deteriorate the measurement accuracy. The problem may be ascribed to a phenomenon of an increase in the temperature of the second pumping cell affecting conduction of electrons of a solid electrolytic layer.

Accordingly, a technique has been developed for making dense a pattern 94a of a heater for heating the sensor element section, which faces a leading-end side of a sensor element 100, and eliminating a pattern 94c from an area corresponding to a second pumping cell (on a rear end of the sensor element 100). In this manner the temperature of the second pumping cell is reduced, to thereby prevent the occurrence of variations in the offset value (see Patent Document 1).

[Patent Document 1] JP-A-10-318979 (a front page, FIG. 3)

3. Problems Solved by the Invention

However, in the technique described in Patent Document 1, the line width of the pattern section 94c removed from the heater is made equal to that of a lead section of the heater. Therefore, this area of the heater does not generate heat and is influenced by external temperatures. Accordingly, the temperature of that area may be changed by an external heat source (e.g., transfer of engine heat from a housing to which the sensor element section is attached), which in turn induces variations in offset value.

SUMMARY OF THE INVENTION

It is therefore an object of the present invention to provide a gas sensor that prevents the occurrence of variations in offset value by changing the configuration of the heater that controls the temperature of the second pumping cell.

The above object has been achieved, in a first (1) aspect of the invention, by providing a gas sensor comprising a longitudinally-extending gas sensor element. The gas sensor element has a first measurement chamber interposed between two solid electrolytic layers stacked with a space therebetween and into which a gas to be measured is introduced from outside the sensor; a first pumping cell that has a first interior pump electrode facing the first measurement chamber and a first counterpart electrode serving as a counterpart electrode of the first interior pump electrode, the first pumping cell being configured to control oxygen partial pressure in the first measurement chamber; a second measurement chamber partitioned from surroundings and in mutual communication with the first measurement chamber and into which a gas to be measured having a controlled oxygen partial pressure is introduced from the first measurement chamber; a second pumping cell having an interior second pumping electrode disposed within the second measurement chamber and a second counterpart electrode serving as a counterpart electrode of the second interior pump electrode, the second pumping cell being configured to detect a specific gas component in the gas to be measured within the second measurement chamber; and a heater which is disposed along the longitudinal direction of gas sensor element, the heater being configured to heat the first pumping cell and the second pumping cell, wherein the heater has a pair of lead sections extending in the longitudinal direction, a first resistance portion that is connected to a leading end of the lead section and that has a higher resistance than the lead sections, and a main heating section which is connected to a leading end of the first resistance portion and which includes a second resistance portion that is disposed on a leading end side in the longitudinal direction relative to a leading end of the first resistance portion and that has a higher resistance than the first resistance portion; the second interior pump electrode does not overlap, in the longitudinal direction, the first interior pump electrode and its first counterpart electrode; and at least a portion of the second interior pump electrode overlaps the first resistance portion in the longitudinal direction.

According to the present invention, a gas sensor is obtained that controls the temperature of the second pumping cell by changing the configuration of the heater, to thus allow for prevention of the occurrence of variations in offset value.

In a preferred embodiment (2) of the gas sensor according to (1) above, a leading end and trailing end of the second interior pump electrode overlap the first resistance portion and the longitudinal direction.

In another preferred embodiment (3) of the gas sensor according to (1) above, a leading end and a trailing end of the first interior pump electrode overlap the second resistance portion in the longitudinal direction.

In yet another preferred embodiment (4) of the gas sensor according to (1) above, the heater is made by coupling at least two or more straight resistance portions extending in a longitudinal direction to a bend portion that connects tie two adjacent straight resistance portions; and the first resistance portion is placed in the straight resistance portion that is positioned outermost in a widthwise direction perpendicular to the longitudinal direction.

In yet another preferred embodiment (5) of the gas sensor according to (4) above, a heating center of the heater in the longitudinal direction is situated in the straight resistance portion within the second resistance portion.

In yet another preferred embodiment (6) of the gas sensor according to (1) above, the main heating section has a third resistance portion that is positioned behind a leading end of the first resistance portion in the longitudinal direction, and the third resistance portion has a lower resistance then the second resistance portion and has a higher resistance then the lead section.

In yet another preferred embodiment (7) of the gas sensor according to (1) above, a difference in resistance between respective portions of the heater comprises a difference in one or more of a line width, a thickness, and a constituent material of the heater.

In yet another preferred embodiment (8) of the gas sensor according to (1) above, a leading end of the gas sensor element in the longitudinal direction is fixed so as to protrude from a housing side of the gas sensors and a relationship of $L \geq 2.4 \times t$ is satisfied, where a length from a stationary end of the gas sensor element to a center of the second pump electrode in the longitudinal direction is taken as L and that the thickness of the gas sensor element is taken as t.

BRIEF DESCRIPTION OF THE DRAWINGS

Illustrative aspects of the present invention will now be described in detail with reference to the drawings, in which.

DETAILED DESCRIPTION OF EXEMPLARY EMBODIMENTS

Embodiments of the present invention will now be described with reference to the drawings. However, the present invention should not be construed as being limited thereto.

Figure 1:
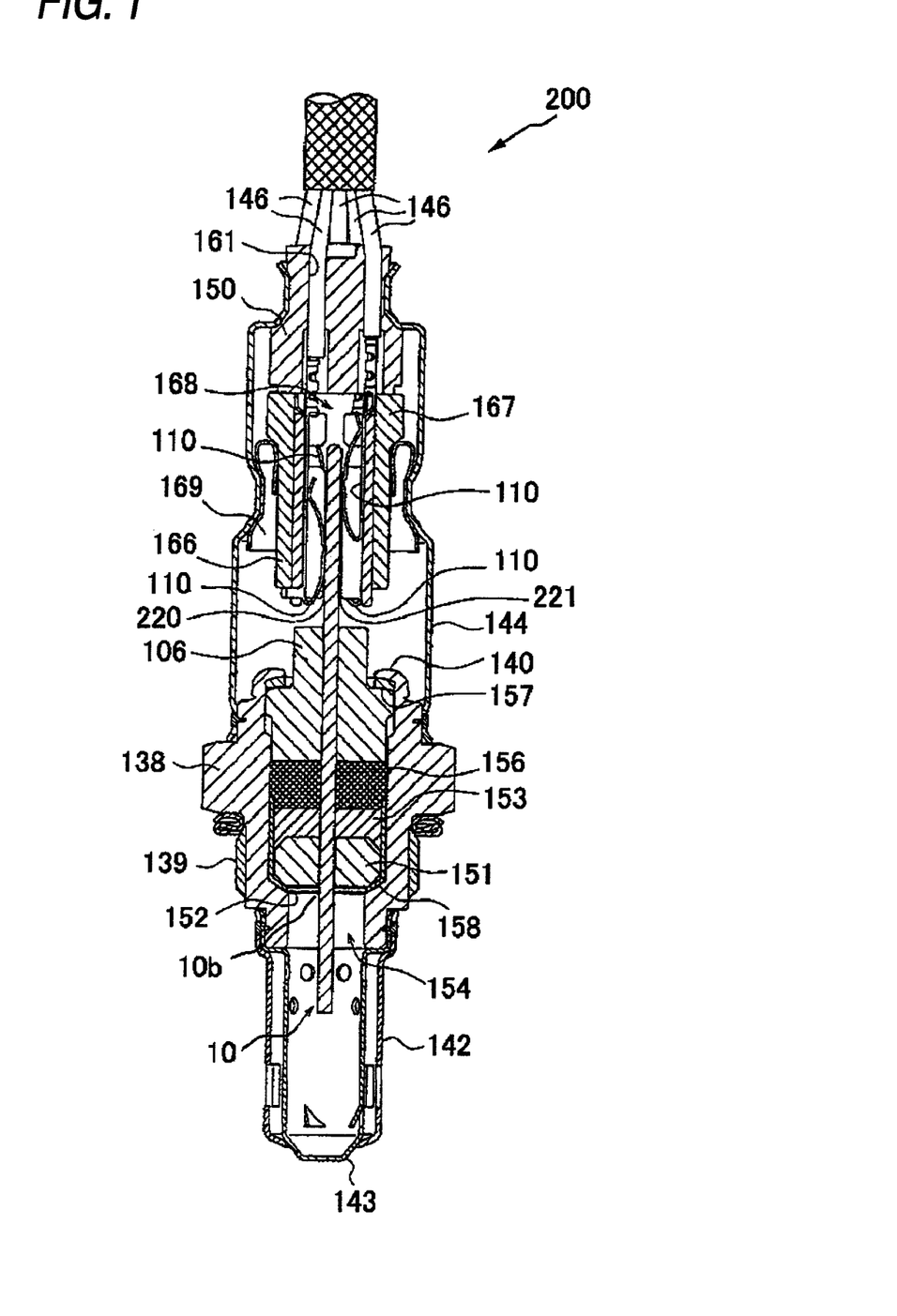
FIG. 1 is a cross-sectional view of an NOx sensor of an exemplary embodiment of the present invention taken along a longitudinal direction.

FIG. 1 shows a cross-sectional view of a gas sensor (an NOx sensor) 200 of a first exemplary embodiment of the present invention taken along a longitudinal direction. The NOx sensor 200 has cylindrical metal shell 138, an exterior surface of which is formed into a thread 139 to be fastened to an exhaust pipe; an NOx sensor element (a gas sensor element) 10 assuming the shape of a plate extending in an axial direction (a longitudinal direction of the NOx sensor 200: a vertical direction in the drawing); a cylindrical ceramic sleeve 106 positioned so as to surround a radial circumference of the NOx sensor element 10; an insulating contact member 166 in which an interior wall surface of a contact insertion hole 168 penetrating through the insulating contact member in an axial direction is arranged so as to surround the circumference of a rear end of the NOx sensor element; and six connection terminals 110 (four connection terminals are illustrated in FIG. 1) interposed between the NOx sensor element 10 and the respective insulation contact members 166.

The metal shell 138 is configured into an essentially-cylindrical shape so as to have a through hole 154 penetrating through the metal shell in an axial direction and a shelf 152 inwardly projecting along the radial direction of the through hole 154. In the metal shell 138, a leading end of the NOx sensor element 10 is positioned outside the leading end side of the through hole 154, and electrode terminal sections 220 and 221 are held in the through hole 154 while positioned outside a rear end side of the through hole 154. Moreover, the shelf 152 is formed as an interiorly-oriented tapered surface that is inclined with respect to a perpendicular plane along the axial direction.

An annular ceramic holder 151, powder-packed layers 153 and 156 (also called talc rings 153 and 156), and the foregoing ceramic sleeve 106 are stacked, in this sequence from the leading end side to the rear end side, within the through hole 154 of the metal shell 138 while surrounding the radial circumference of the NOx sensor element 10. A crimp packing 157 is interposed between the ceramic sleeve 106 and a rear end section 140 of the metal shell 138. A metal holder 158 that holds the talc ring 153 and the ceramic holder 151 and that maintains airtightness is interposed between the ceramic holder 151 and the shelf 152 of the metal shell 138. The rear end section 140 of the metal shell 138 is crimped so as to press the ceramic sleeve 106 toward the leading end side by way of the crimping packing 157.

In the first exemplary embodiment, the NOx sensor element 10 is fastened by means of the ceramic holder 151, or the like, that constitutes the housing of the gas sensor 200, and the NOx sensor element 10 protrudes from a lower surface of the ceramic holder 151. Accordingly, an area of the NOx sensor element 10 located at the same position where the lower surface of the ceramic holder 151 is situated is taken as a stationary end 10b.

As shown in FIG. 1, an outer metal protector 142 and an inner metal protector 143, which cover a projecting portion of the NOx sensor element 10 and which have a plurality of pores, are doubly attached to an outer periphery of the leading end (a lower portion shown in FIG. 1) of the metal shell 138 by means of welding or the like.

An outer sheath 144 is fixed to an outer periphery of the rear end of the metal shell 138. A grommet 150 is disposed in an opening of the rear end side (an upper position in FIG. 1) of the outer sheath 144. The grommet 150 has lead wire insertion holes 161 into which six lead wires 146 (only five of them are shown in FIG. 1) electrically connected to the electrode terminal sections 220 and 221 of the NOx sensor element 10 are inserted.

An insulating contact member 166 is positioned at the rear end (an upper portion shown in FIG. 1) of the NOx sensor element 10 projecting out of the rear end 140 of the metal shell 138. The insulating contact member 166 is placed around the electrode terminal sections 220 and 221 formed on the surface of the rear end of the NOx sensor element 10 The insulating contact member 166 is formed into a cylindrical shape having a contact insertion hole 168 that penetrates through the insulating contact member in the axial direction, and also has a collar 167 projecting from an outer surface of the insulating contact member 166 to the radial outside. The insulating contact member 166 is positioned within the outer sheath 144 as a result of the collar 167 contacting the outer sheath 144 by way of a holding member 169.

The structure of the NOx sensor element 10 will now be described by reference to a cross-sectional view of FIG. 2 taken along a longitudinal direction. In the first exemplary embodiment, the term "longitudinal direction" means a longitudinal direction of the NOx sensor element and a direction perpendicular to a direction in which the respective layers of the NOx sensor element are stacked.

Figure 2:
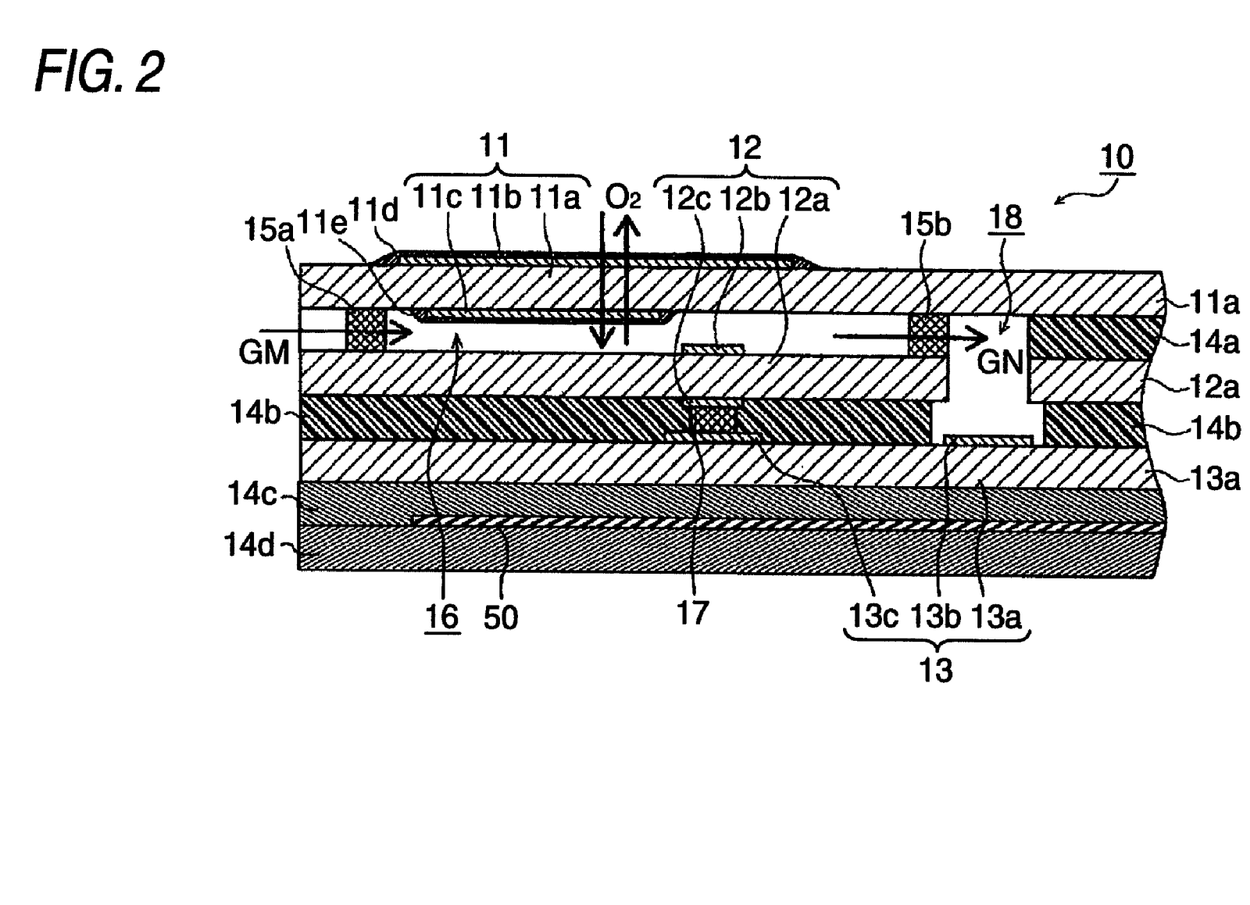
FIG. 2 is a cross-sectional view of the NOx sensor element taken along its longitudinal direction.

In FIG. 2, the NOx sensor element 10 has a structure in which a first solid electrolytic layer 11a, an insulation layer 14a, a second solid electrolytic layer 12a, an insulation layer 14b, a third solid electrolytic layer 13a, and insulation layers 14c and 14d are stacked in this sequence A first measurement chamber 16 is partitioned between the first solid electrolytic layer 11a and the second solid electrolytic layer 12a. A gas to be measured GM is introduced from the outside by way of a first diffusive resistance element 15a positioned at the left end (an entrance) of the first measurement chamber 16.

A second diffusive resistance element 15b is positioned at a location on the first measurement chamber 16 opposite the entrance. A second measurement chamber 18 in mutual communication with the first measurement chamber 16 is partitioned in an area on the right side of tie first measurement chamber 16 by way of the second diffusive resistance element 15b. The second measurement chamber 18 is formed between the first solid electrolytic layer 11a and the third solid electrolytic layer 13a while penetrating through the second solid electrolytic layer 12a.

An elongated plate-shaped heater 50 that extends along the longitudinal direction of the NOx sensor element 10 is embedded between the insulation layers 14c and 14d. The heater 50 heats the gas sensor to an activation temperature and enhances conductivity of oxygen ions in the solid electrolytic layer, to thereby stabilize operation.

The insulation layers 14a to 14d are primarily made of alumina, and the first diffusive resistance element 15a and the second diffusive resistance element 15b are made of a porous substance, such as alumina. In addition, the heater 50 is made of platinum, or the like.

A first pumping cell 11 has a first solid electrolytic layer 11a primarily made of zirconia exhibiting oxygen ion conductivity, and a first interior pump electrode 11c and a first counterpart electrode (a first exterior pump electrode) 11b which are positioned such that the first solid electrolytic layer 11a is sandwiched between the electrodes 11b and 11c; and the first interior pump electrode 11c faces the first measurement chamber 16. Both the first interior pump electrode 11c and the first exterior pump electrode 11b are primarily made of platinum, and the surfaces of the respective electrodes are coated with protective layers 11e and 11d made of a porous substance.

An oxygen concentration detection cell 12 has a second solid electrolytic layer 12a primarily made of zirconia, and a detection electrode 12b and a reference electrode 12c disposed such that the electrolytic layer 12a is sandwiched between the electrodes 12b and 12c. The detection electrode 12b is located downstream of the first interior pump electrode 11c and faces the first measurement chamber 16. Both the detection electrode 12b and the reference electrode 12c are primarily made of platinum.

A cutout is formed in the insulation layer 14b such that the reference electrode 12c contacting the second solid electrolytic layer 12a is disposed therein. Further, the resultant space is filled with a porous substance, thereby constituting a reference oxygen chamber 17. A predetermined feeble current is preliminarily passed through to the oxygen concentration detection cell 12. In this manner, oxygen is supplied to the reference oxygen chamber 17 from the first measurement chamber 16, to thereby provide an oxygen standard.

The second pumping cell 13 has a third solid electrolytic layer 13a primarily made of zirconia, a second interior pump electrode 13b, and a second counterpart electrode 13c which is a counterpart electrode of the second interior pump electrode 13b. The second interior pump electrode 13b that is placed at an area on the surface of the third solid electrolytic layer 13a facing the second measurement chamber 18 Both the second interior pump electrode 13b and the second counterpart pump electrode 13c are primarily made of platinum.

The second counterpart pump electrode 13c is placed at a cutout of the insulation layer 14b on the third solid electrolytic layer 13a and faces the reference oxygen chamber 17 while positioned opposite the reference electrode 12c.

When the solid electrolytic layers 11a to 13a are viewed from a direction perpendicular to the longitudinal direction as well as in a direction perpendicular to the direction in which the layers are stacked, the second interior electrode pump 13b does not overlap the first interior pump electrode 11c and the first exterior pump electrode 11b along the longitudinal direction. The reason for this is that, as described below, an aspect of the present invention resides in controlling the temperature of the second interior pump electrode 13b (i.e., the second pumping cell 13) so as to become lower than the temperature of the first pumping cell 11 and in separately controlling the temperature of the first pumping cell 11 and the temperature of the second pumping cell 13.

Next, an exemplary operation of the NOx sensor element 10 will be described. First, when power is externally supplied as a result of starting of the engine, the heater 50 is activated by way of a predetermined control circuit, thereby heating the first pumping cell 11, the oxygen concentration detection cell 12, and the second pumping cell 13 to an activation temperature. When the respective cells 11 to 13 are heated to the activation temperature, the first pumping cell 11 pumps excess oxygen in the gas to be measured (an exhaust gas) GM, which has flowed into the first measurement chamber 16, from the first interior pump electrode 11c toward the first counterpart electrode 11b.

Since the concentration of oxygen in the first measurement chamber 16 achieved at this time is responsive to an interelectrode voltage (a terminal voltage) Vs of the oxygen concentration detection cell 12, an interelectrode voltage (a terminal voltage) Vp1 of the first pumping cell 11 is controlled such that the interelectrode voltage Vs becomes a constant voltage V1 (e.g., 425 mV), thereby adjusting (generally, lowering) the concentration of oxygen in the first measurement chamber 16 to an extent at which NOx is not decomposed.

The gas to be measured GN whose oxygen concentration has been adjusted further flows toward the second measurement chamber 18. A constant voltage Vp2 (a voltage that is higher than a control voltage of the oxygen concentration detection cell 12; for instance, 450 mV) at which the NOx gas in the gas to be measured GN is decomposed into oxygen and an $N_2$ gas is applied as an interelectrode voltage (a terminal voltage) Vp2 of the second pumping cell 13, whereupon NOx is decomposed into nitrogen and oxygen. A second pump current Ip2 flows into the second pumping cell 13 in such a way that the oxygen resulting from decomposition of NOx is pumped out of the second measurement chamber 18. Since a linear relationship exists between the second pump current Ip2 and the NOx concentration at this time, the NOx concentration in tie gas to be measured can be detected by monitoring Ip2.

Figure 3A:
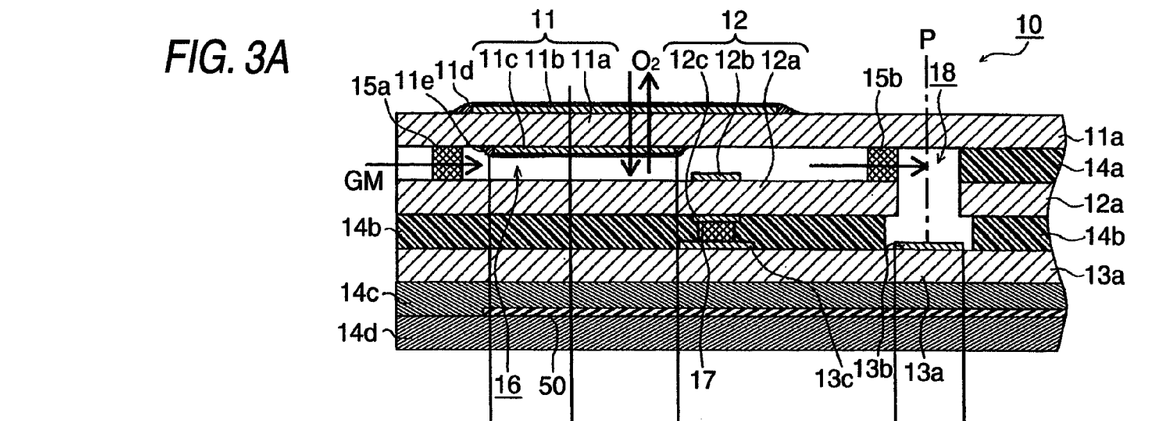
FIGS. 3A and 3B are views showing the shape and arrangement of a heater.
Figure 3B:
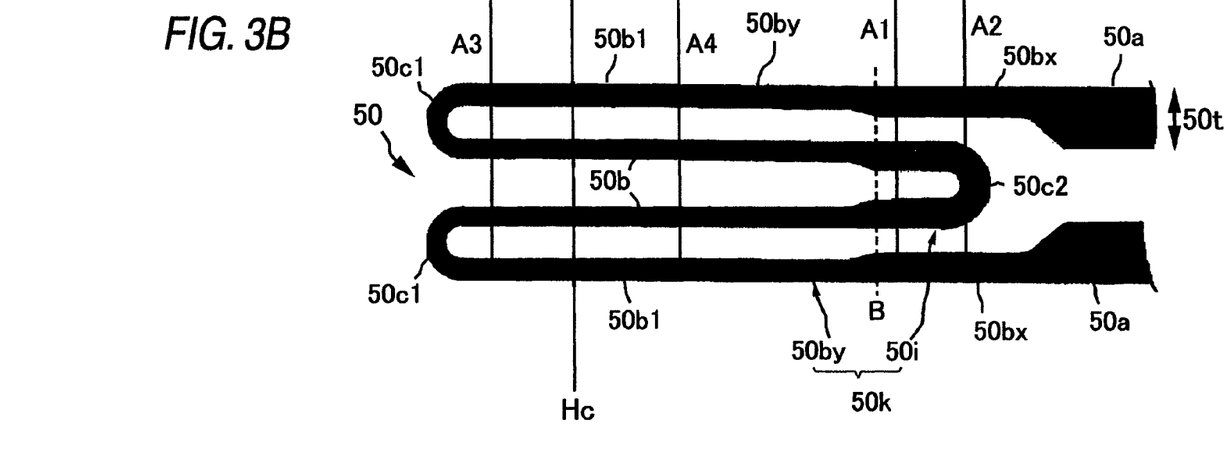

FIG. 3 shows the shape and layout of the heater. FIG. 3A shows a cross-sectional view of the NOx sensor element 10 identical to that of FIG. 2. FIG. 3B shows a plan view of a heater 50. Straight lines A1, A2, A3, A4 and Hc extending between FIGS. 3A and 3B show a positional correspondence between respective constituent elements of the NOx sensor element 10 and the heater 50.

In FIG. 3B, the heater 50 is constructed by connecting together lead portions 50*a*, straight resistance portions 50*b* and 50*b*1 extending in a longitudinal direction (identical with the longitudinal direction of the NOx sensor element 10), and bends 50*c*1 and 50*c*2 coupling the two adjacent straight resistance portions.

More specifically, in the heater 50, one lead portion 50*a* is connected to a lead-end side bent portion 50*c*1 by way of the straight resistance portion 50*b*1. The leading-end side bend 50*c*1, which has a reverse bend in the longitudinal direction, is connected to the straight resistance portion 50*b*. The straight resistance portion 50*b* is connected to the rear-end side bend 50*c*2. The rear-end side bend 50*c*2, which has a reverse bend in the longitudinal direction, is connected to the other straight resistance portion 50*b*. The other straight resistance portion 50*b* is connected to the other leading-end side bend 50*c*1. The other leading-end side bend 50*c*1, which has reverse bend in the longitudinal direction, is connected to the other straight resistance portion 50*b*1, and the other straight resistance portion 50*b*1 is connected to the other lead portion 50*a*.

The straight resistance portion 50*b*1 is connected to the lead portion 50*a* and has a first resistance portion 50*bx* whose width is narrower than that of the lead portion 50*a*.

Moreover, the second interior pump electrode 13*b* is situated so as to be aligned within the first resistance portion 50*bx* in the longitudinal direction. More specifically, the leading end and the trailing end of the second interior pump electrode 13*b* overlap the first resistance portion 50*bx* in the longitudinal direction (corresponding to A1 and A2 in FIG. 3). A center P of the second interior pump electrode 13*b* with respect to the longitudinal direction also overlaps tie first resistance portion 50*bx* in the longitudinal direction.

The first resistance portion 50*bx* can control the temperature of the second interior pump electrode 13*b* by situating the second interior pump electrode 13*b* within the first resistance portion 50*bx*.

Considering the second pumping cell 13, the second counterpart pump electrode 13*c* is located outside the projection of the first resistance portion 50*bx*. However, the location where NOx, H$_2$O and other gases are decomposed is above the second interior pump electrode 13*b*. Hence, the essential requirement is to control the temperature of the second interior pump electrode 13*b*.

Moreover, since the first resistance portion 50*bx* becomes higher than the lead portion 50*a* in terms of resistance as a result of the first resistance portion 50*bx* being made narrower than the lead portion 50*a*, the first resistance portion 50*bx* is reliably heated, so that the second interior pump electrode 13*b* can be controlled to a predetermined temperature.

Further, the first resistance portion 50*bx* is connected to a main heating portion 50*k*, and the main heating portion 50*k* extends over the straight resistance portions 50*b* and 50*b*1 and the bends 50*c*1 and 50*c*2. The main heating portion 50*k* has a second resistance portion 50*by* located ahead of the leading end (a position B in FIG. 3) of the first resistance portion 50*bx* and a third resistance portion 50*i* located behind the leading end of the first resistance portion 50*bx*. Of these resistance portions, the second resistance portion 50*by* is made narrower than the first resistance portion 50*bx* and overlaps the first interior pump electrode 11*c* in the longitudinal direction. More specifically, the leading end and the trailing end of the first interior pump electrode 11*c* overlap the second resistance portion 50*by* in the longitudinal direction (as indicated by A3 and A4 in FIG. 3).

As a result of the second resistance portion 50*by* being made narrower than the first resistance portion 50*bx* as mentioned above, the second resistance portion 50*by* has a higher resistance than the first resistance portion 50*bx*, whereby the heating action of the second resistance portion 50*by* is more intense. Hence, the temperature of the first resistance portion 50*bx* can be set so as to become lower than the temperature of the second resistance portion 50*by*. Consequently the second interior pump electrode 13*b* is controlled to a lower temperature, to thereby prevent the occurrence of variations in offset value. It is therefore possible to prevent the occurrence of a deficiency in oxygen pumping capacity and variations in offset value, which would otherwise occur when a decrease in temperature of the first pumping cell 11 overlapping the second resistance portion 50*by* arises in the longitudinal direction, by heating the second resistance portion 50*by* to a higher temperature.

Moreover, the leading end and the trailing end of the second interior pump electrode 13*b* desirably overlap the first resistance portion 50*bx* in the longitudinal direction. As a result, the entirety of the second interior pump electrode 13*b* overlaps the first resistance portion 50*bx* in the longitudinal direction, so that the temperature of the second interior pump electrode 13*b* can be controlled more reliably by the first resistance portion 50*bx*.

Further, the leading end and the trailing end of the first interior pump electrode 11*c* desirably overlap the second resistance portion 50*by* in the longitudinal direction. As a result, the entirety of the first interior pump electrode 11*c* overlaps the second resistance portion 50*by* in the longitudinal direction. In this manner, it becomes possible to further prevent the occurrence of a deficiency in oxygen pumping capability and variations in offset values which would otherwise occur when the temperature of the first pumping cell 11 becomes lower.

The respective bends 50*c*1 and 50*c*2 are present among the longitudinally-extended straight resistance portions 50*b* and 50*b*1. Therefore, when compared with a case where the straight resistance portions extend in the widthwise direction of the NOx sensor element 10 which is shorter than tie longitudinal direction of the NOx sensor element 10 (50*t* in FIG. 3B), the lengths of the straight resistance portions 50*b* and 50*b*1 are made comparatively longer, and the number of bends can be reduced accordingly. Hence, there is little chance of local overheating arising in the bends 50*c*1 and 50*c*2, so that tie durability of the heater 50 can be enhanced.

In addition to changing the line width of lie heater 50 as mentioned above, changing the thickness the heater 50 and changing tie material of the heater 50 are also possible as a method for changing the resistance of the respective sections of the heater 50. Alternatively, two or more of these methods may be combined together. Adding a component exhibiting high electrical conductivity (low specific resistance) to the material of the heater 50 (for instance, adding Au or Ag to Pt that is the principal constituent of the heater 50), to thus reduce resistance, can be mentioned as a method for changing the material of the heater 50. Additionally, adding a component exhibiting low electrical conductivity (large specific resistance) to the material of the heater 50 (for instance, adding one or more of aluminum, zirconia, ceria, yttria, Rh, Pd, Ir, Ru, Os, and Cu to Pt that is the principal constituent of the heater 50), to thus increase resistance, can also be mentioned.

Moreover, it is desirable that a heating center Hc of the heater 50 be situated at the straight resistance portions 50$b$1 and 50$b$ in the second resistance portion 50$by$ in the longitudinal direction.

The heating center Hc of the heater 50 refers to the maximum temperature area of the heater 50 when viewed in a given direction (the longitudinal direction of the gas sensor element 10 (=the heater 50) of the first exemplary embodiment). The center area of the heater 50 is usually hottest, and the temperature of the heater decreases with increasing distance toward an edge of the heater.

By adopting such a configuration, the bends 50$c$1 and 50$c$2 are not present in the heating center Hc of the heater 50 that becomes hottest. In this manner, the occurrence of local overheating in the bends 50$c$1 and 50$c$2 is further inhibited and durability of the heater 50 can be further enhanced. Moreover, since the heating center Hc is present in the straight resistance portions 50$b$1 and 50$b$, heat is dissipated to a certain extent while the heat is transferred from the heating center Hc to the bends 50$c$1 and 50$c$2, whereupon overheating of the bends 50$c$1 and 50$c$2 is prevented.

The third resistance portion 50$i$ of the main heating portion 50$k$ is lower in resistance than the second resistance portion 50$by$ and higher in resistance than the lead portion 50$a$. As a result of such a configuration, the third resistance portion 50$i$ situated within the second interior pump electrode 13$b$ is also made higher in resistance than the lead portion 50$a$. Hence, the third resistance portion 50$i$ is reliably heated, and the second interior pump electrode 13$b$ can be controlled to a predetermined temperature. Further, since the third resistance portion 50$i$s lower in resistance than the second resistance portion 50$by$, the temperature of the third resistance portion 50$i$ can be made lower than the second resistance portion 50$by$. Thus, the second interior pump electrode 13$b$ can be controlled to a lower temperature, whereby the occurrence of variations in offset value can be prevented.

As shown in the Examples below, the present inventors found that when the temperature of the second pumping cell 13 exceeds 650° C., a second pump current Ip2 resulting from dissociation of water develops, which in turn causes further variation in offset value. For this reason, the heater 50 is desirably controlled such that the temperature of the second interior pump electrode 13$b$ constituting the second pumping cell 13 is maintained at 400 to 650° C. The reason for increasing the temperature of the second pumping cell 13 to 400° C. or higher is that when the temperature decreases to 400° C. or lower, the NOx dissolving power of the second interior pump electrode 13$b$ becomes deficient.

Likewise, as shown in the Examples below, the present inventors found that, when the temperature of the first pumping cell 11 exceeds 850° C., electron conduction of the solid electrolytic layer is enhanced, thereby decreasing the offset value. For this reason, it is preferable to control the heater 50 such that the temperature of the first pumping cell 11 is maintained at 700 to 850° C. The reason for increasing the temperature of the first pumping cell 11 to 700° C. or higher is that, when the temperature is decreased to 700° C. or lower, ion conductivity of the solid electrolytic layer is decreased, which in turn results in a deficiency in oxygen pumping capability.

Figure 4:
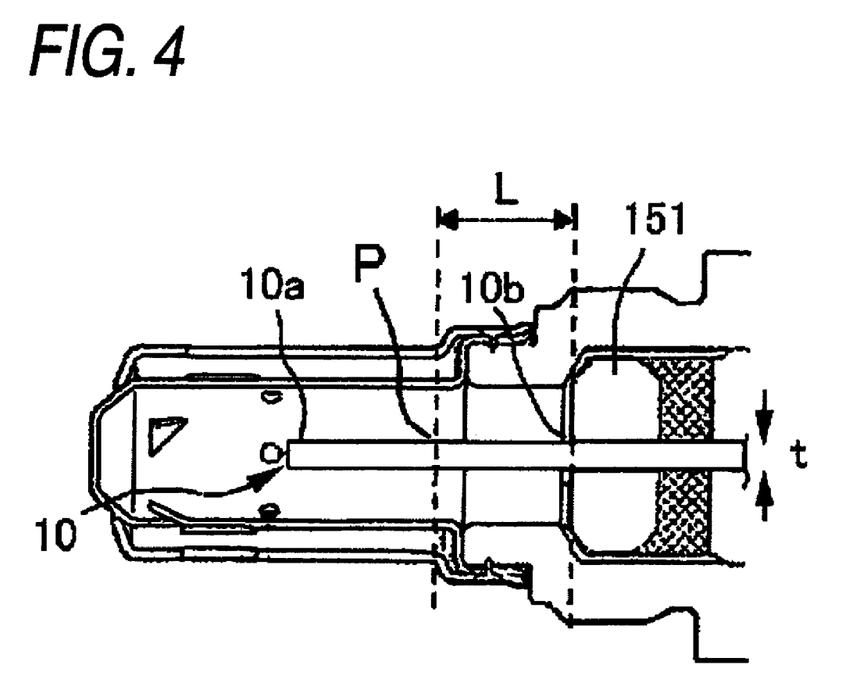
FIG. 4 is a partially-enlarged view of FIG. 1.

FIG. 4 is a partially-enlarged view of FIG. 1, showing a positional relationship between the housing (the ceramic holder 151) of the NOx sensor and the gas sensor element 10. Provided that a distance from the stationary end 10$b$ of the NOx sensor element to the center P of the second interior pump electrode 13$b$ in the longitudinal direction of the NOx sensor element 10 is taken as L and that the thickness of the NOx sensor element is taken as "t," a relationship of $L \geq 2.4 \times t$ is preferably satisfied.

Normally, a hot gas to be measured (an exhaust gas) transfers heat from the outside (Hex: the collar of the metal shell 138) of the NOx sensor 10 to the NOx sensor element hold section (the ceramic holder 151) in the housing, and the heat further travels to the NOx sensor element 10. Accordingly, in order to prevent the second pumping cell 13 from being heated by the heat transferred from the gas to be measured, the distance from the ceramic holder 151 to the second interior pump electrode 13$b$ is preferably made longer.

As shown in the Examples below, the present inventors found that when a relationship of $L \geq 2.4 \times t$ is satisfied, an increase in the temperature of the second pumping cell 13 can be prevented even when the second pumping cell is exposed to the hot gas to be measured.

The present invention will be described in yet further detail below by reference to the following Examples. However, the present invention should not be construed as being limited thereto.

EXAMPLE 1

An NOx sensor 200 of a first exemplary embodiment was manufactured according to an ordinary method. The heater 50 was made by applying a paste principally made of Pt and sintering the paste, and the resistance of respective sections of the heater 50 was changed by changing the line widths of the heater 50.

Power was applied to the heater 50 by use of the NOx sensor 200, thereby controlling the voltage of the heater such that the temperature of the second pumping cell 13 (the second interior pump electrode 13$b$) reached a predetermined temperature. After elapse of 30 minutes from the time that power was applied to the heater 50, an output of the second pump current Ip2 was acquired for 30 seconds while a total quantity of 18 liters of a gas containing 0% $O_2$, 10% $H_2O$ and a balance of $N_2$ (a gas temperature of 120° C.) was caused to flow to the sensor. Then, an average of the outputs was taken as an offset value (an offset current).

Figure 5:
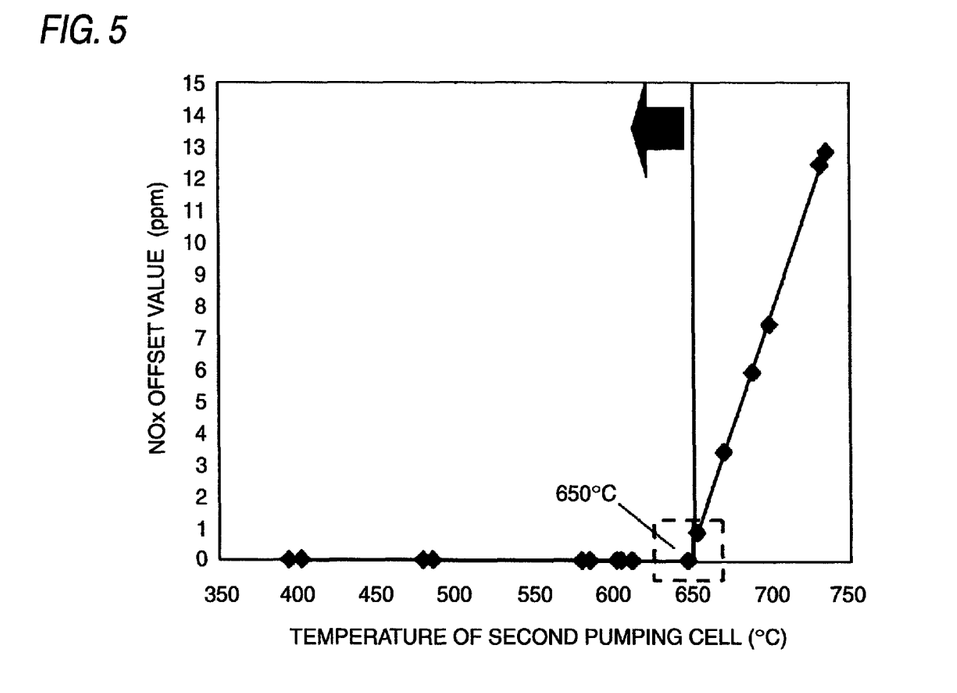
FIG. 5 is a view showing changes in offset value with a change in the temperature of a second pumping cell.

FIG. 5 shows the variation in offset value with a change in temperature of the second pumping cell 13. As shown in FIG. 5, an offset current starts to flow when the temperature of the second pumping cell 13 exceeds 650° C. This is conceivably ascribable to dissociation of water present in the gas.

EXAMPLE 2

The output of the second pump current Ip2 was acquired for 30 seconds in the same manner as in Example 1, except that the gas component was changed to 0% $O_2$, 0.1% $H_2O$, 100 ppm NO and a balance of $N_2$, and an average of the output was taken as an NOx gain.

Figure 6:
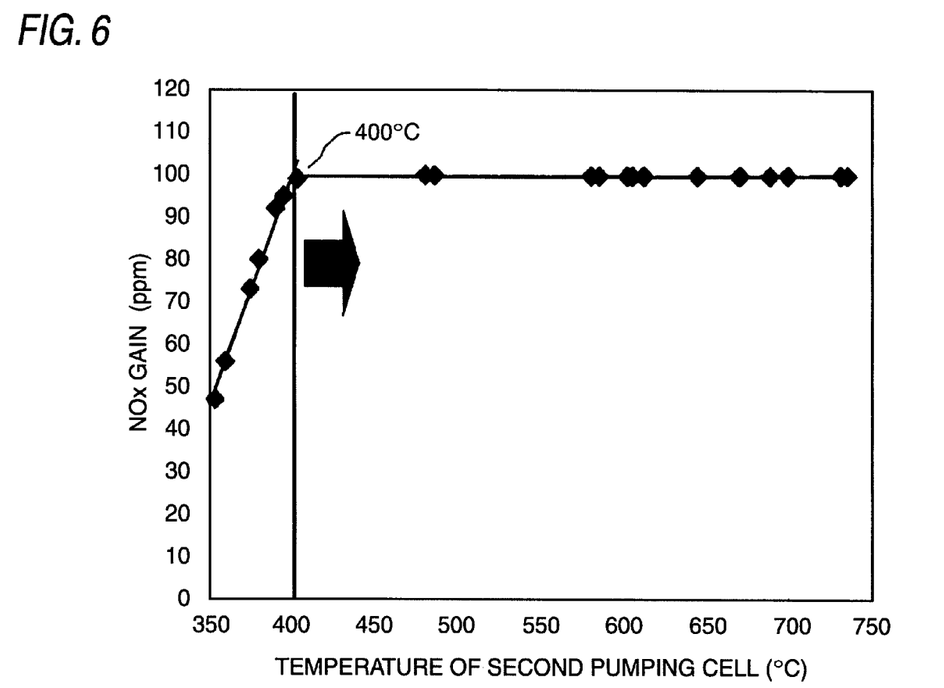
FIG. 6 is a view showing changes in NOx gain with a change in the temperature of the second pumping cell.

FIG. 6 shows the change in NOx gain with a change in the temperature of the second pumping cell 13. As shown in FIG. 6, when the temperature of the second pumping cell 13 was less than 400° C., a decrease in NOx gain and a reduction in NOx decomposition power of the second pumping cell 13 was observed.

Based on the results of Examples 1 and 2, the temperature of the second pumping cell 13 is preferably controlled to 400 to 650° C.

EXAMPLE 3

The output of the second pump current Ip2 was acquired for 30 seconds in the same manner as in Example 1, except that the gas component was changed to 0.1% $H_2O$, 16% $O_2$ and a balance of $N_2$; except that the temperature of the second pumping cell 13 was held constant at a 580° C.; and except that the temperature of the first pumping cell 11 was changed. An average of the output was taken as an offset value.

Figure 7:
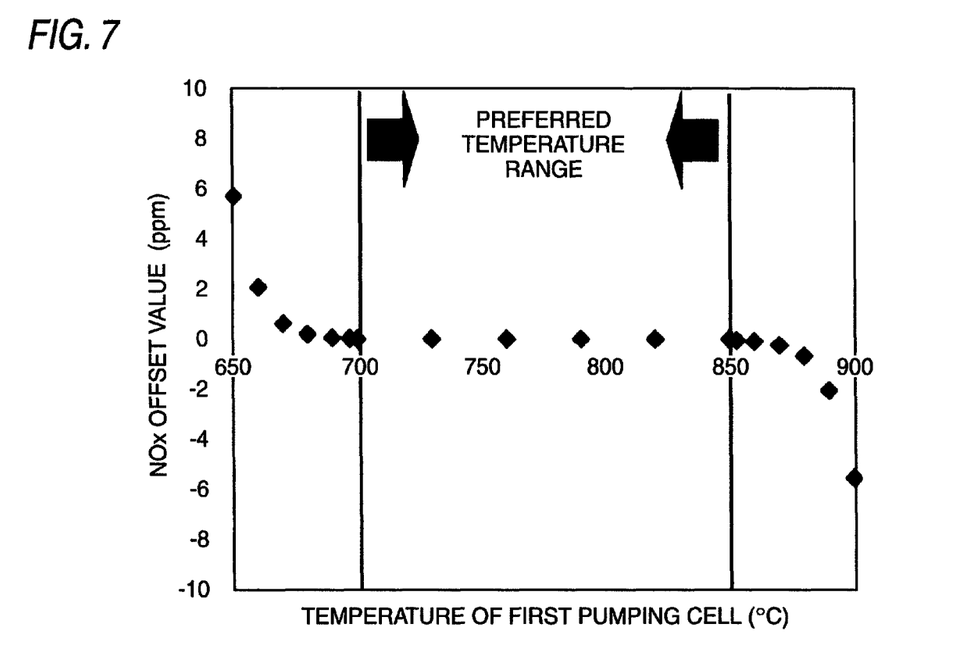
FIG. 7 is a view showing changes in offset value achieved with a change in the temperature of a first pumping cell.

FIG. 7 shows the change in offset value within a change in the temperature of the first pumping cell 11. When the temperature of the first pumping cell was 700° C. or less, the offset current increased. The reason for this is a deficiency in oxygen pumping capability. In the meantime, when the temperature of the first pumping cell 11 exceeded 850° C., the offset current decreased. A conceivable reason for this result is that the gradient of oxygen concentration in the first measurement chamber abruptly increased. This is because oxygen pumping performed on an output side (the trailing end) became predominant as a result of an increase in contribution of electron conduction of an input side (a leading end side) of the first pumping cell 11.

According to Example 3, the temperature of the first pumping cell 11 is preferably controlled to 700 to 850° C.

EXAMPLE 4

A plurality of NOx sensors were manufactured in the same manner as in Example 1, with variously changing the length L of the NOx sensor element. After ten minutes had elapsed during which the outside of the Hex (the metal shell 138) of each of the NOx sensors was held at 500° C., the temperature of a position spaced the length L was measured. In relation to the dimension of the ceramic holder 151, the diameter of the ceramic holder is 10.4 mm, and an axial length of the same is about 4.6 mm; and the thickness "t" of the NOx sensor element is 1.5 mm.

Figure 8:
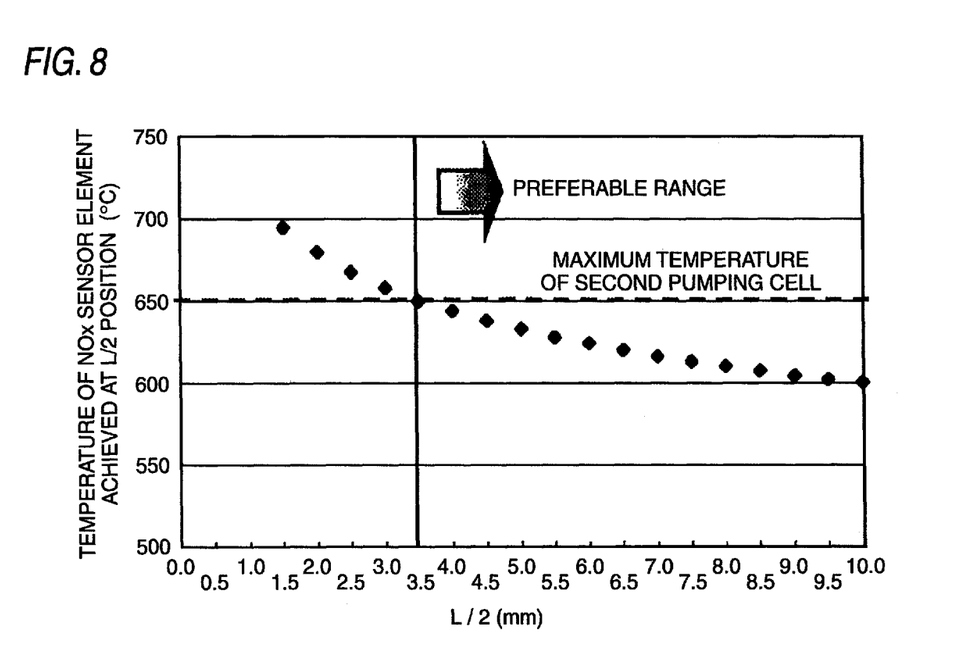
FIG. 8 is a view showing the temperature of a position L/2 achieved with a change in the length L/2 of the NOx sensor element.

Table 8 shows the thus-acquired results. In the case of L=3.5 mm or greater, the temperature of the second pumping cell 13 dropped to 650° C. or less. From these results, the relationship $L \geq 2.4 \times t$ is preferably satisfied.

The present invention is not limited to the above Examples, and covers various modifications and equivalents. For instance, the planar geometry of the heater is not limited to those mentioned above.

In relation to the Examples, the solid electrolytic layers 11a, 12a and 13a that constitute the NOx sensor element 10 are embodied as three layers; however, the layers may also be embodied as two layers. The structure of an NOx sensor element having two solid electrolytic layers is described, for instance, in JP-A-2004-354400 (FIG. 3).

The present invention can be applied to a gas sensor for detecting the concentration of NOx gas in an exhaust gas from an automobile or various internal combustion engines or a combustion gas from a boiler, an oxygen sensor such as an all range air-fuel sensors or the like, and the invention is not limited to these applications. For instance, the present invention can also be applied to a gas sensor having a gas sensor element for measuring the concentration of a gas (e.g., $CO_x$, $H_2O$, HC, or the like) other than NOx.

According to the above exemplary embodiment, a gas sensor is provided comprising a longitudinally-extending gas sensor element. The gas sensor element has a first measurement chamber that is partitioned between two solid electrolytic layers stacked with a space therebetween and into which a gas to be measured is introduced from outside the gas sensor; a first pumping cell that has a first interior pump electrode facing tie first measurement chamber and a first counterpart electrode serving as a counterpart electrode of the first interior pump electrode, tie first pumping cell controlling oxygen partial pressure in tie first measurement chamber; a second measurement chamber partitioned from surroundings and in mutual communication with tie first measurement chamber and into which a gas to be measured having a controlled oxygen partial pressure is introduced from the first measurement chamber; a second pumping cell having an interior second pumping electrode disposed within the second measurement chamber and a second counterpart electrode of the second interior pump electrode and that detects a specific gas component in the gas to be measured within the second measurement chamber; and a heater that is positioned along a direction in which the solid electrolytic layers are stacked and that heats the first pumping cell and the second pumping cell, wherein tie heater has a pair of lead sections extending in tie longitudinal direction, a first resistance portion that is connected to a leading end of the lead section and that has a higher resistance than the lead sections, a second resistance portion that is disposed on a leading end side in the longitudinal direction relative to a leading end of the first resistance portion and that has a higher resistance than the first resistance portion, and a main heating section that is connected to a leading end of the first resistance portion; the second interior pump electrode does not overlap, in the longitudinal direction, the first interior pump electrode and its first counterpart electrode; and at least a portion of the second interior pump electrode overlaps the first resistance portion in the longitudinal direction.

By adopting such a configuration, the second interior pump electrode and tie first resistance portion overlap each other in the longitudinal direction, so that tie temperature of the second interior pump electrode (i.e., the second pumping cell) can be controlled by the first resistance portion.

Incidentally, if the first resistance portion and the lead section have the same resistance, the first resistance portion will not generate heat. Hence, the first resistance portion is influenced by the external temperature, which makes it difficult to control the second interior pump electrode to a predetermined temperature. In contrast, in the present invention, the first resistance portion is made to have a higher resistance than the lead portion. Hence, the first resistance portion reliably generates heat, whereby the second interior pump electrode can be controlled to a predetermined temperature.

Moreover, since the second resistance portion is made to have a higher resistance than the first resistance portion, heat generation of the second resistance portion becomes more intensive, and the temperature of the first resistance portion can be made lower than the temperature of the second resistance portion. Consequently, tie temperature of the second interior pump electrode is controlled to a low temperature, so that the occurrence of variations in offset value can be prevented. Alternatively, the occurrence of variations in offset value (which would otherwise arise when oxygen pumping capability becomes deficient as a result of the temperature of the first pumping cell overlapping the second resistance portion in the longitudinal direction becoming lower) can be prevented by increasing the temperature of the second resistance portion.

In the above exemplary embodiment, the word "resistance" means resistance per unit length.

Further, the word "leading end side in a longitudinal direction" means to a side that is closer to the first pumping cell than to the second pumping cell when viewed in the longitudinal direction. The word "behind in a longitudinal direction" refers to a direction opposite that side.

The leading end and the trailing end of the second interior pump electrode preferably overlap the first resistance portion in the longitudinal direction. As a result, the entirety of the second interior pump electrode overlaps the first resistance portion in the longitudinal direction. Whereby the temperature of the second interior pump electrode (i.e., the second pumping cell) can be reliably controlled by the first resistance portion.

The leading end and the trailing end of the first interior pump electrode preferably overlap the second resistance portion in the longitudinal direction. As a result, the entirety of the first interior pump electrode overlaps the second resistance portion in the longitudinal direction, whereby the occurrence of variations in offset value, which would otherwise arise when oxygen pumping capability becomes deficient as a result of the temperature of the first pumping cell becoming lower, can be further prevented.

The heater is preferably made by coupling at least two or more straight resistance portions extending in the longitudinal direction to a bend that connects the two adjacent straight resistance portions; and the first resistance portion is placed in the straight resistance portion that is positioned outermost in a widthwise direction perpendicular to the longitudinal direction. When an internal temperature of the heater is changed by making the pattern of the heater dense and coarse, the durability of the heater deteriorates. The reason is that, since the curvature of a bend in a heater line becomes larger at a dense area in the pattern (a radial value becomes smaller), the inside of the bend locally generates heat, to thus become easily broken in a short period of time. In contrast, the bend is reached by way of the straight resistance section that extends in a longitudinal direction. Therefore, when compared with a case where a straight resistance section extends in a widthwise direction of the NOx sensor element 10 which is shorter than the longitudinal direction of the NOx sensor element 10, the straight resistance portion can be made comparatively longer, and the number of bends can be reduced accordingly. Hence, the chance of occurrence of local heat generation of the bend becomes small, and durability of the heater can be enhanced.

The heating center of the heater in the longitudinal direction is preferably situated in the straight resistance portion within the second resistance portion.

By means of such a configuration, the bend is not situated at the heating center of the heater where the highest heat is realized. Hence, local overheating in the bend is further inhibited, and durability of the heater can be further enhanced. Moreover, since the heating center lies in the straight resistance portion, heat is dissipated to a certain extent during a period in which heat transfers from the heating center to the bend, so that overheating of the bend is prevented.

Here, the heating center of the heater refers to the maximum temperature area of the heater when viewed from a certain direction. The center of the heater is usually hottest, and the temperature decreases with increasing distance from the center to a periphery of the heater.

The main heating section preferably has a third resistance portion that is positioned behind a leading end of the first resistance portion in the longitudinal direction, and the third resistance portion has a lower resistance than the second resistance portion and has a higher resistance than the lead section. By means of such a configuration, even the third resistance portion situated in the second interior pump electrode is made to have a higher resistance than the lead portion. Hence, the third resistance portion reliably generates heat, and the second interior pump electrode can be controlled to a predetermined temperature. Moreover, since the third resistance portion is made to have a lower resistance than the second resistance portion, the temperature of tie third resistance portion can be made lower than the temperature of the second resistance portion. Thus, the occurrence of variations in offset value can be prevented by controlling the second interior pump electrode to a lower temperature.

The resistance of the heater is preferably changed by changing at least one or more of a line width, a thickness, and a material of the heater. This makes it possible to readily change the resistance of the heater (resistance per unit length).

The leading end of the gas sensor element in the longitudinal direction is preferably fixed so as to protrude from a housing side of the gas sensors and a relationship of $L \geqq 2.4 \times t$ is preferably satisfied, provided that a length from a stationary end of the gas sensor element to a center of the second pump electrode in the longitudinal direction is taken as L and that the thickness of the gas sensor element is taken as "t."

By means of such a configuration, even when the gas sensor is exposed to a hot gas to be measured, an increase in the temperature of the second pumping cell can be prevented. In relation to the hot gas to be measured, heat usually travels from the outside of the housing of the gas sensor to the gas sensor element stationary section in the housing and further to the gas sensor element. Accordingly, in order to prevent an increase in the temperature of the second pumping cell, which would otherwise be caused by transfer of heat from the gas to be measured, the distance from the stationary section of the gas sensor element to the center (the position L) of the second pump electrode is preferably made longer.

It should further be apparent to those skilled in the art that various changes in form and detail of the invention as shown and described above may be made. It is intended that such changes be included within the spirit and scope of the claims appended hereto.

This application is based on Japanese Patent Application No. 2008-095640 filed on Apr. 2, 2008 and Japanese Patent Application No. 2009-036296 filed on Feb. 19, 2009, the above-identified applications incorporated herein by reference in their entirety.

What is claimed is:
1. A gas sensor comprising:
a gas sensor element extending in a longitudinal direction thereof and having a leading end, the gas sensor comprising at the leading end of the gas sensor element:
a first measurement chamber interposed between two solid-state electrolytic layers stacked with a space therebetween and into which a gas to be measured is introduced from outside the sensor;
a first pumping cell that has a first interior pump electrode facing the first measurement chamber and a first counterpart electrode serving as a counterpart electrode of the first interior pump electrode, the first pumping cell being configured to control oxygen partial pressure in the first measurement chamber;
a second measurement chamber partitioned from surroundings and in mutual communication with the first measurement chamber and into which a gas to be measured having a controlled oxygen partial pressure is introduced from the first measurement chamber;
a second pumping cell having an interior second pumping electrode disposed within the second measurement chamber and a second counterpart electrode serving as a counterpart electrode of the second interior pump electrode, the second pumping cell being configured to detect a specific gas component in the gas to be measured within the second measurement chamber; and
a heater which is disposed along the longitudinal direction of gas sensor element, the heater being configured to heat the first pumping cell and the second pumping cell, wherein
the heater has first and second lead sections extending in the longitudinal direction, each of said first and second lead sections having a trailing end for electrical connection to a power source and a leading end, two parallel first resistance portions extending in the longitudinal direction, each having a leading end and a trailing end electrically connected to the leading end of the first and second lead sections, respectively, said first resistance portions having a higher resistance than the lead sections to which they are connected, and a main heating section which electrically connects the leading ends of the two parallel first resistance portions, and which main heating section includes two parallel second resistance portions that are disposed on a leading end side of the gas sensor element in the longitudinal direction relative to the leading ends of the two parallel first resistance portions, respectively;

the second interior pump electrode does not overlap, in the longitudinal direction, the first interior pump electrode and its first counterpart electrode; and at least a portion of the second interior pump electrode overlaps the first resistance portion in the longitudinal direction.

2. The gas sensor according to claim 1,
wherein a leading end and a trailing end of the second interior pump electrode overlap the first resistance portion in the longitudinal direction.

3. The gas sensor according to claim 1,
wherein a leading end and a trailing end of the first interior pump electrode overlap the second resistance portion in the longitudinal direction.

4. The gas sensor according to claim 1,
wherein the heater comprises at least two or more adjacent and coupled straight resistance portions extending in the longitudinal direction to a bend portion that connects the two adjacent straight resistance portions; and
the straight resistance portion that is positioned outermost in a widthwise direction perpendicular to the longitudinal direction comprises one of said first resistance portions.

5. The gas sensor according to claim 4,
wherein a heating center of the heater in the longitudinal direction is situated in a straight resistance portion within the second resistance portions.

6. The gas sensor according to claim 1,
wherein the main heating section has a third resistance portion that is positioned behind a leading end of the first resistance portion in the longitudinal direction, and the third resistance portion has a lower resistance than the second resistance portions and a higher resistance than the lead section.

7. The gas sensor according to claim 1,
wherein a difference in resistance between respective portions of the heater comprises a difference in one or more of a line width, a thickness and a constituent material of the heater.

8. The gas sensor according to claim 1,
wherein a leading end of the gas sensor element in the longitudinal direction is fixed so as to protrude from a housing side of the gas sensor, and
a relationship of $L \geqq 2.4 \times t$ is satisfied, where a length from a stationary end of the gas sensor element to a center of the second pump electrode in the longitudinal direction is taken as L and that the thickness of the gas sensor element is taken as t.

* * * * *